United States Patent
Thompson et al.

(10) Patent No.: US 9,752,993 B1
(45) Date of Patent: Sep. 5, 2017

(54) NONDESTRUCTIVE EVALUATION OF RAILROAD RAILS, WHEELS, AND AXLES

(71) Applicant: The Boeing Company, Chicago, IL (US)

(72) Inventors: Jeffrey G. Thompson, Auburn, WA (US); John R. Hull, Sammamish, WA (US); Morteza Safai, Newcastle, WA (US); Barry A. Fetzer, Renton, WA (US); Gary E. Georgeson, Tacoma, WA (US); Steven K. Brady, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/265,509

(22) Filed: Sep. 14, 2016

(51) Int. Cl.
| | |
|---|---|
| *G01N 21/95* | (2006.01) |
| *G01N 21/88* | (2006.01) |
| *G01M 17/10* | (2006.01) |
| *G01M 7/02* | (2006.01) |
| *B61L 23/04* | (2006.01) |

(52) U.S. Cl.
CPC ........ *G01N 21/8851* (2013.01); *B61L 23/044* (2013.01); *B61L 23/045* (2013.01); *G01M 7/025* (2013.01); *G01M 17/10* (2013.01); *G01N 21/95* (2013.01)

(58) Field of Classification Search
CPC .. G01N 21/8851; G01N 21/95; B61L 23/044; B61L 23/045; G01M 7/025; G01M 17/10
See application file for complete search history.

(56) References Cited

U.S. PATENT DOCUMENTS

| | | | | |
|---|---|---|---|---|
| 4,955,236 | A * | 9/1990 | Yokoyama | G01M 7/025 250/342 |
| 5,149,025 | A * | 9/1992 | Utterback | B61K 9/06 246/169 A |
| 5,335,995 | A * | 8/1994 | Villar | F16F 1/374 248/634 |
| 5,677,533 | A * | 10/1997 | Yaktine | B61K 9/04 246/169 A |
| 5,870,192 | A | 2/1999 | Barker | |
| 6,399,948 | B1 | 6/2002 | Thomas et al. | |
| 7,075,084 | B2 | 7/2006 | Thompson et al. | |
| 7,119,338 | B2 | 10/2006 | Thompson et al. | |
| 7,295,321 | B1 | 11/2007 | Marshall et al. | |
| 8,806,950 | B2 | 8/2014 | Hull et al. | |
| 2009/0049936 | A1 * | 2/2009 | Mian | G01M 17/10 73/865.8 |
| 2013/0191070 | A1 * | 7/2013 | Kainer | B61K 9/08 702/167 |
| 2014/0316719 | A1 * | 10/2014 | Lanza di Scalea | G01M 5/0025 702/42 |

* cited by examiner

*Primary Examiner* — Marcus Taningco
(74) *Attorney, Agent, or Firm* — Thompson Hine LLP

(57) ABSTRACT

A system for nondestructive evaluation of railroad rails, includes a carriage including a plurality of wheels movably supporting the carriage on the rails, a source of vibration mounted on the carriage and connected to transmit vibrations of a preselected frequency to test regions on the rails through the wheels to cause an increase in temperature of the rails at locations of flaws in the test regions, an infrared detector for recording thermal images of the test regions to detect the increase in temperature of the location of the flaws, a controller connected to actuate the infrared detector to record the thermal images of the vibrations impacting the test regions, and store the thermal images recorded by the infrared detector.

20 Claims, 4 Drawing Sheets

NONDESTRUCTIVE EVALUATION OF RAILROAD RAILS, WHEELS, AND AXLES

TECHNICAL FIELD

The disclosure relates to nondestructive evaluation systems and methods, and more particularly, to systems and methods for the nondestructive evaluation of railroad rails, wheels, and axles.

BACKGROUND

It is necessary to maintain the integrity of structural objects and components that have been subjected to wear and stress from the hazards of the environment in which such objects and components operate. Accordingly, it is desirable to test such structural objects and components periodically to determine whether they have degraded strength or reliability due to such flaws as surface cracks, corrosion, disbonds, and the like. While in some instances it is possible to remove the object to be tested from its location of use and perform a test of its integrity while it is mounted on a test stand in a laboratory using laboratory instruments, this is not always possible or practicable. In many instances, the test object is very large and/or is integrated into a larger structure in a manner that makes its removal difficult if not impossible to remove for remote testing in a laboratory.

Further, it is desirable to perform nondestructive evaluation (NDE) tests on objects. An advantage of NDE tests is that they do not permanently alter an object in an undesirable manner, which may render the test object useless for its intended purpose. Consequently, there is a need to develop methods and systems for NDE tests on objects without having to remove the objects from their location and environment of use.

Nondestructive evaluation systems and methods have been developed to provide non-contact inspection of components and structures in the field to detect flaws and otherwise determine the integrity of such structures and components. One form of NDE is thermographic inspection, in which a thermal pattern at the test object's surface is created and differences in the surface temperature are interpreted to determine the existence of flaws. One type of active thermographic inspection is infrared thermography. A form of infrared thermography is vibrothermography, which uses amplitude modulated or pulses of ultrasonic waves to excite internal features of the test object. A source or mechanical vibration transmits ultrasonic vibrations in the test object, which cause the surfaces defining the flaw or defect to vibrate at different frequencies relative to each other creating heat. The heat generated at the location of the flaw raises the temperature of the test object at the flaw above that of the remainder of the test object. This area of greater temperature is apparent on a thermal image of the test object taken by an infrared camera. The locations of the defects are thus detected by infrared cameras through the process of mapping temperature distribution on the surface of the object.

A disadvantage with such systems is that they are static. That is, they require structure that places them in close proximity with the object to be tested, and that object must not be moving to enable the system and method to be performed on a specific test area. Such systems may be appropriate for non-moving objects, such as parked vehicles and aircraft. However, there is a need for a method and system for nondestructive evaluation of moving vehicles, such as railroad cars, and for traversing extremely large objects, such as railroad rails.

SUMMARY

The disclosed system for nondestructive evaluation may be utilized for NDE of the rails of rail systems, as well as for the NDE of the wheels and axles of railcars. With respect to railroad rails, the test system may be mounted on a movable vehicle so that the railroad rails may be tested on a continuous basis. This greatly reduces the time and expense required for nondestructive evaluation of long, elongate objects such as railroad rails. In one embodiment, a system for nondestructive evaluation of railroad rails includes a carriage having a plurality of wheels movably supporting the carriage on the rails, a source of vibration mounted on the carriage and connected to transmit vibrations of a preselected frequency to test regions on the rails through the wheels to cause an increase in temperature of the rails at locations of flaws in the test regions, an infrared detector for recording thermal images of the test regions to detect the increase in temperature at the locations of the flaws, and a controller connected to actuate the infrared detector to record the thermal images of the vibrations impacting the test regions, and store the thermal images recorded by the infrared detector.

In another embodiment, a system for nondestructive evaluation of a wheel assembly on a railcar includes a pair of rails, each having an excitation segment with a source of vibration connected to transmit vibrations of a preselected frequency to test regions on the wheel assembly to cause an increase in temperature of the wheel assembly at locations of flaws in the test regions, an infrared detector for recording thermal images of the test regions to detect the increase in temperature at the locations of the flaws, and a controller connected to actuate the infrared detector to record the thermal images of the vibrations impacting test regions, and store the thermal images recorded by the infrared detector.

In yet another embodiment, a method for nondestructive evaluation of railroad rails includes moving a carriage having a plurality of wheels on the rails, transmitting vibrations of a preselected frequency to test regions on the rails through the wheels by a source of vibration mounted on the carriage, the vibrations causing an increase in temperature of the rails at locations of flaws in the test regions, recording thermal images by an infrared detector of the test regions to detect the increase in temperature at the locations of flaws, and actuating the infrared detector by a controller to record the thermal images of the vibrations impacting the test regions, and storing the thermal images recorded by the infrared detector.

In still another embodiment, a method for nondestructive evaluation of a wheel assembly on a railcar includes moving a carriage over excitation segments of a pair of rails, transmitting vibrations of a preselected frequency by a source of vibration to test regions on the wheel assembly to cause an increase in temperature of the wheel assembly at locations of the flaws in the test regions, recording by an infrared detector thermal images of the test regions to detect the increase in temperature of the locations of the flaws, and actuating by a controller the infrared detector to record the thermal images of the vibrations impacting test regions, and storing the thermal images recorded by the infrared detector.

Other objects and advantages of the disclosed nondestructive evaluation system and method will be apparent from the following description, the accompanying drawings, and the appended claims.

DETAILED DESCRIPTION

Figure 1:
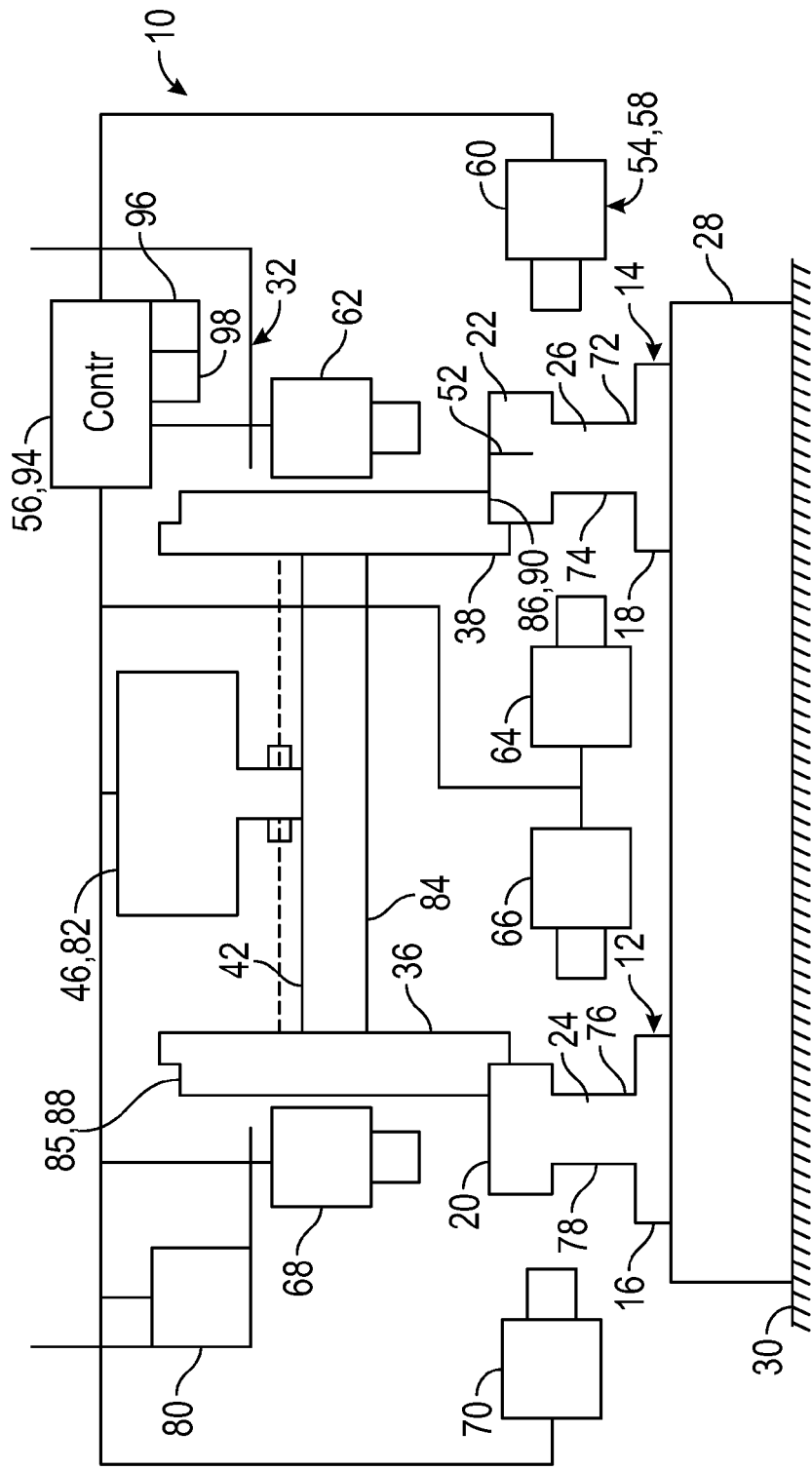
FIG. 1 is a schematic end elevation of an embodiment of the disclosed system for nondestructive evaluation of railroad rails.
Figure 2:
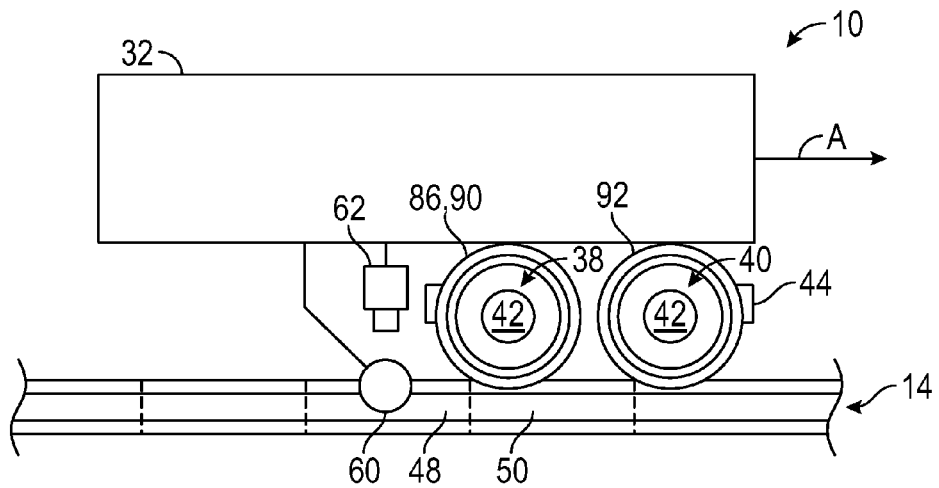
FIG. 2 is a schematic, side elevation of the system of FIG. 1.

As shown in FIGS. 1 and 2, a system, generally designated 10, may be utilized for the nondestructive evaluation (NDE) of railroad rails 12, 14. Railroad rails 12, 14 each may have flat bottoms 16, 18, heads 20, 22 and webs 24, 26, respectively, joining the heads with the bottoms. The rails 12, 14 may be mounted on ties 28 (only one of which is shown in FIG. 1) that, in turn, may be mounted on ballast 30. The system 10 may include a carriage, generally designated 32, that may include a plurality of wheels, which may include wheels 36, 38 shown in FIG. 1, and wheels 38, 40 in FIG. 2. The wheels 36, 38 may be mounted on an axle 42 that may be attached to the carriage 32 by a truck 44 (FIG. 2).

A source of vibration 46 may be mounted on the carriage 32 and connected to transmit vibrations of a preselected frequency to test regions 48, 50 on the rails 12, 14 through the wheels 36, 38 to cause an increase in temperature of the rails at locations of flaws 52. In embodiments, the source of vibration 46 may take the form of an ultrasonic welder, such as an ultrasonic welder operating at a minimum of 400 watts. The frequency of the vibration may be selected from between 10 kHz and 40 kHz, dependent on the structure and material of the railroad rails 12, 14. In embodiments, the selected frequency may take the form of swept frequencies, for example vibrations at frequencies sweeping between 10 kHz and 40 kHz, which may be likely to cause a resonance in the railroad rails 12, 14. Only test regions 48, 50 for rail 14 are shown in FIG. 2, it being understood that corresponding test regions, not shown, exist directly across on rail 12. Although two test regions 48, 50 are shown in FIG. 2, test regions may be designated all along the lengths of rails 12, 14, and in embodiments adjacent test regions may be contiguous, as are test regions 48, 50 along the lengths of the rails 12, 14 under study.

Figure 8:
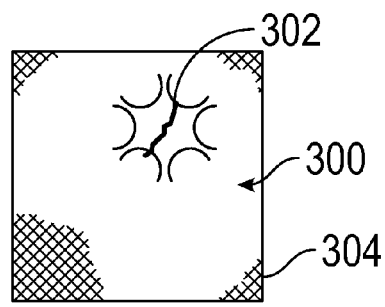
FIG. 8 is a representative thermal image showing a flaw as a bright line.

An infrared detector, generally designated 54, may be positioned to record thermal images of the test regions 48, 50 to detect the increase in temperature at the locations of the flaws 52 as a result of heat generated by the vibrations from the source of vibrations 46. In an embodiment, a flaw 52 may take the form of a break in the surface of the rail 12. A representative example of such a thermal image 300 is shown in FIG. 8. The presence of a flaw 52 (FIG. 1) may appear as a bright line 302 approximating the shape and location of the flaw in the rail 12 against a relatively dark or black background 304. The system 10 also may include a controller 56 connected to actuate the infrared detector 54 to record the thermal images of the vibrations impacting the test regions 48, 50, and store the thermal images recorded by the infrared detector.

In an embodiment, the infrared detector 54 may take the form of an array, generally designated 58, of infrared cameras 60, 62, 64, 66, 68, and 70 mounted on and movable with the railcar 32. Specifically, infrared camera 60 is oriented to record an image of an outside web portion 72 of rail 14, camera 62 is oriented to record an image of an upper surface of the head portion 22 of rail 14, camera 64 is oriented to record an image of an inside web portion 74 of rail 14, camera 66 is oriented to record an image of an inside web portion 76 of rail 12, camera 68 is oriented to record a thermal image of the upper surface of the head portion 20 of rail 12, and camera 70 is oriented to record an image of an outside web portion 78 of rail 12. The cameras 60-70 may be mounted on the carriage 32 so that movement of the carriage relative to the rails 12, 14 also moves the camera 60-70 of the array 58. In embodiments, cameras 60, 64, 66, and 70 may be oriented to record images of the bottoms 16, 18 of the rails 12, 14 instead or in addition to imaging webs 24, 26 of the rails 12, 14.

The carriage or railcar 32 may include an onboard motor 80 that may be actuated by the controller 56, or by an operator, to move the railcar in the direction of arrow A in FIG. 2 over the rails 12, 14 so that the array 58 of the infrared detector 54 passes over the test regions 48, 50. In an alternate embodiment, the carriage would not have a motor 80, but would rather be pushed or pulled by an outside motive force, such as a traction engine (not shown). In an embodiment, the source of vibration 46 may take the form of an ultrasonic transducer 82 that contacts a component 84 of the carriage 32. The ultrasonic transducer 82 may be connected such that the controller 56 actuates the ultrasonic transducer to transmit the vibrations through the component 84 to the test regions 48, 50 of the rails 12, 14. In an embodiment, the component 84 may be selected from the wheels 36, 38 and/or the axle 42 connected to the wheels and attached to a remainder of the carriage 32, which may be by way of truck 44.

Alternatively, or in addition, in embodiments, the source of vibration 46 may take the form of one or more of the plurality of wheels, for example wheels 36, 38, having peripheries 85, 86 sufficiently rough to cause the vibrations in the test regions 48, 50 of a preselected frequency when the railcar 32 moves relative to the rails 12, 14 at a preselected speed. For example, the wheels 36, 38 may have peripheries 85, 86 that include transverse grooves or ridges spaced and shaped to create a vibration in excess of 1 kilohertz as the railcar 32 moves at a speed of 25 miles per hour over the rails 12, 14. This frequency may be selected to maximize the temperature increase at the flaw or flaws 52 in the rails 12, 14 so that the thermal images 300 captured by the infrared detector 54 will show bright spots 302 coinciding with the flaws 52 (FIG. 8). In another embodiment, the peripheries 85, 86 of the wheels 36, 38 may have segmented surfaces 88, 90.

In embodiments, the wheels, such as wheels 38, 40 (as well as corresponding wheels, of which wheel 36 is one, on an opposite side of railcar 32 that engage rail 12), may have peripheries 86, 92 with segmented surfaces arranged to generate the vibrations in the rails 12, 14 as the carriage 32 moves relative to the rails. The segmented surfaces of the peripheries 86, 92 may be oriented such that they are out of phase with each other, and the preselected frequency may be selected to be greater than 1 kilohertz (kHz).

In an embodiment, the controller 56 may include a data store 94 for storing the recorded thermal images by the infrared detector 54. Also in an embodiment, the controller 56 may include a visible light camera 96 connected to be actuated by the controller for photographing the test regions 48, 50, for purposed of determining false positives by the detector 54 and/or for identifying the rail test region 48, 50 containing the flaw 52. The controller may be programmed to actuate the visible light camera 96 only when a flaw 52 is detected in one of the rails 12, 14. The controller 56 also may include a global positioning system (GPS) 98 that may be connected to record a location of a flaw 52 in one or both of the rails 12, 14 detected by the infrared detector 54.

Figure 3:
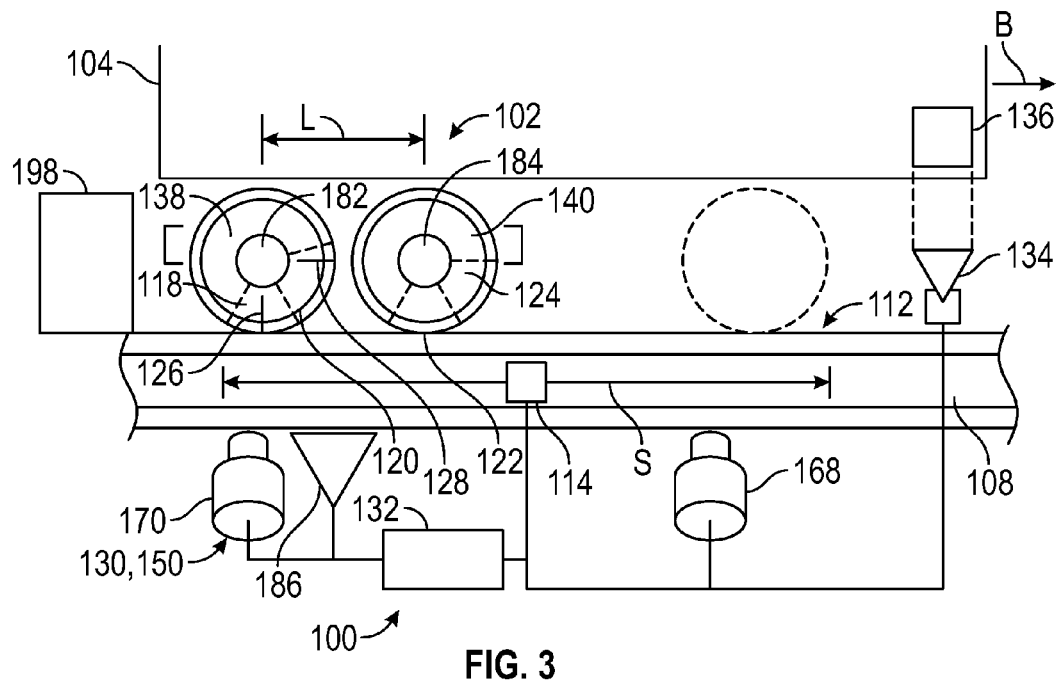
FIG. 3 is a schematic, side elevation of another embodiment of the system for nondestructive evaluation of railroad wheels and axles.
Figure 4:
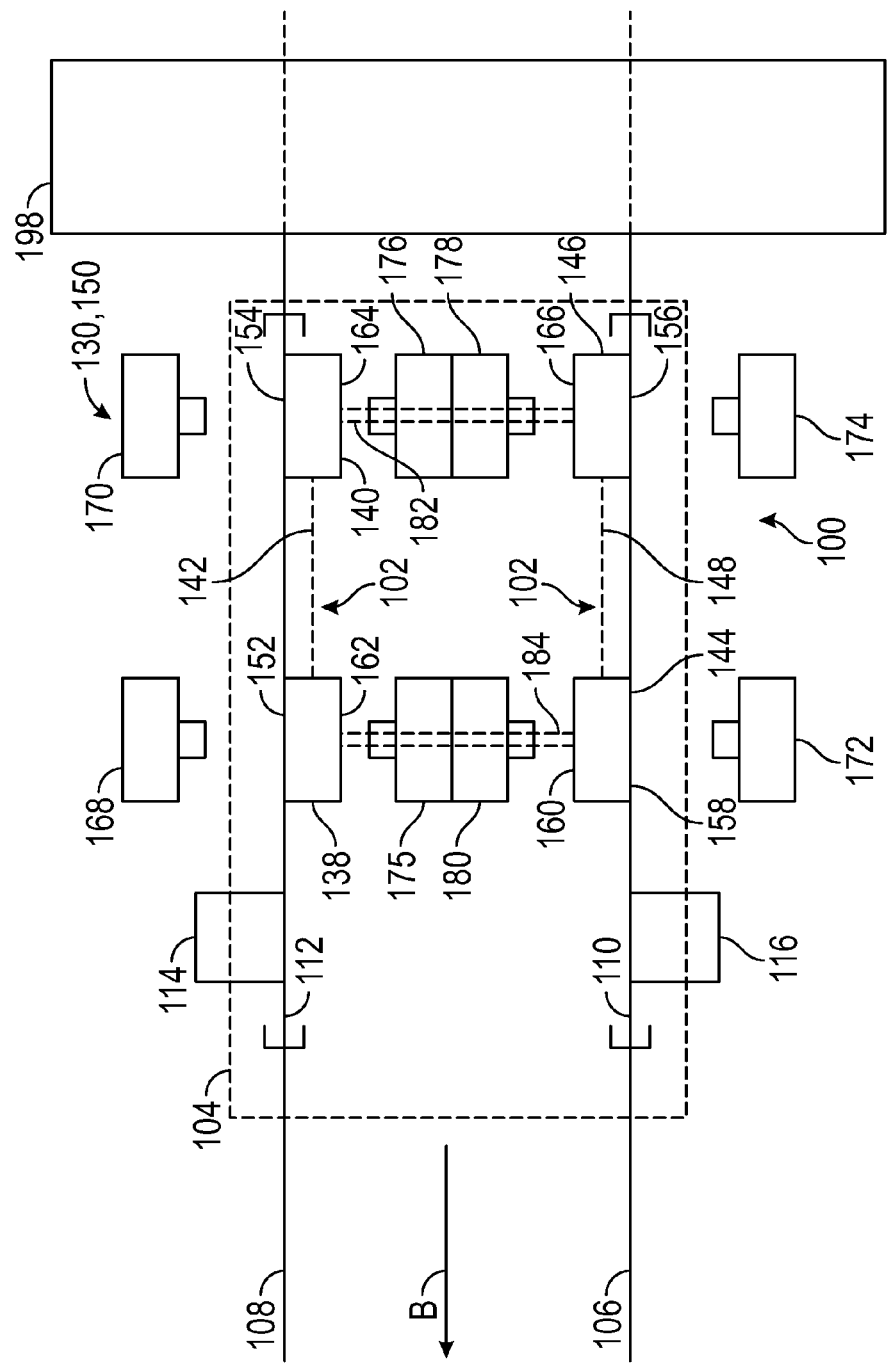
FIG. 4 is a schematic plan view of the system of FIG. 3.

As shown in FIGS. 3 and 4, in another embodiment, a system, generally designated 100, for nondestructive evaluation of a wheel assembly, generally designated 102, on a railcar 104 may include a pair of rails 106, 108, each having an excitation segment 110, 112, which may include a source of vibration 114, 116 connected to transmit vibrations of a preselected frequency sequentially to test regions 118, 120 of wheel 138 and to test regions 122, 124 of wheel 140 on the wheel assembly 102 to cause an increase in temperature of the wheel assembly at locations of flaws 126, 128 in the test regions. The system 100 also may include an infrared detector 130 for recording thermal images 300 (FIG. 8) of the test regions 118-124 to detect the increase in temperature at the locations of flaws 126, 128.

The system 100 also may include a controller 132 connected to actuate the infrared detector 130 to record the thermal images 300 of the vibrations impacting the test regions 118-124, and store the thermal images recorded by the infrared detector. The system also may include a visible light camera 134 connected to be actuated by the controller 132 to record an image of the railcar 104 having the wheel assembly 102 for which thermal images are recorded.

In an embodiment, the railcar 104 may include a unique indicia 136, which may take the form of a barcode or other alphanumeric code, that may uniquely identify the railcar and may be located at a predetermined position on a side of the railcar. The visible light camera 134 may photograph the indicia 136 for purposes of identifying the railcar 104 as having a wheel assembly 102 with wheels 138, 140 having flaws 126, 128. As shown in FIG. 4, the railcar 104 may include wheel assembly 102, which may take the form of wheels 138, 140 that may be mounted on a truck 142 on one side of the railcar, and similarly, wheels 144, 146 on an opposite side of the railcar 104, which may be mounted on a truck 148, and ride on rail 106. In embodiments, trucks 142 and 148 may take the form of a single truck on which wheels 138, 140, 144, and 146 are rotatably mounted, and which is rotatably mounted on railcar 104.

In an embodiment, the infrared detector 130 may take the form of an array, generally designated 150, of infrared cameras positioned to record thermal images of the outboard faces 152, 154, 156, 158 of wheels 138, 140, 146, 144, respectively, of the wheel assembly 102, and inboard faces 160, 162, 164, 166, of the wheels 144, 138, 140, 146, respectively, as the wheels pass over the excitation segments 110, 112 of the rails 106, 108. In an embodiment, the array 150 of infrared cameras may be arranged along the lengths of the excitation segments 110, 112 sufficient to record images of entire circumferences of two sets of the wheels 138, 140 and 144, 146 on railroad trucks 142, 148, respectively.

In a particular embodiment, the array 150 may include infrared cameras 168, 170, 172, 174 positioned to record thermal images of the outboard faces 152, 154, 156, and 158 of wheels 138, 140, 144, 146. Similarly, the array 150 may include infrared cameras 175, 176 positioned to take infrared images of the inboard surfaces 162, 164 of wheels 138, 140, respectively, and cameras 178, 180 positioned to take thermal images of the inboard surfaces 166, 160 of wheels 146, 144, respectively.

In an alternate embodiment, the infrared detector 130 may include an array 150 of infrared cameras that may include cameras 168-180 positioned to record thermal images of the axles 182, 184 of the wheel assembly 102 as the axles pass over the excitation segments 110, 112. Also in embodiments, the system 100 may include a marker 186 that may be actuated by the controller 132. The marker may take the form of a dye marker, ink jet sprayer, or other device for depositing a substance on a selected wheel 138, 140 that may have a flaw 126, 128 that is detected by the system 100. The marker 186 may be positioned to deposit the marking substance on either one of the wheels 138, 140, for example, or on an axle, such as axles 182, 184. In the embodiment in which the system 100 is configured to detect flaws in the axles 182, 184, the infrared cameras 175, 176, 178, 180 may be positioned beneath the axles on ties and oriented to point upwardly so that they may take images of the axles from beneath.

In the embodiment shown in FIGS. 3 and 4, the source of vibration 114, 116, may take the form of an ultrasonic transducer or transducers connected to the rails 106, 108 to transmit vibrations to the excitation segments 110, 112 of the rails. The ultrasonic transducers 114, 116 may be connected to be actuated by the controller 132 to transmit the vibrations to the test regions 118, 120, 122, 124, for example, of the wheel assemblies 102 when the test regions contact the excitation segments. Additionally, or in the alternative, as shown in FIG. 5 the source of vibration may include the excitation segments 110', 112' having upper surfaces 190 with grooves 192 formed transversely therein and shaped such that movement of the wheels 138, 140, 144, 146 of the railcar 104 over the grooves at a predetermined speed causes the vibrations in the wheel assemblies 102 that create temperature increases at flaws 126, 128 that are imaged by the thermal images 300 (FIG. 8) taken by the infrared detector 130.

Figure 5:
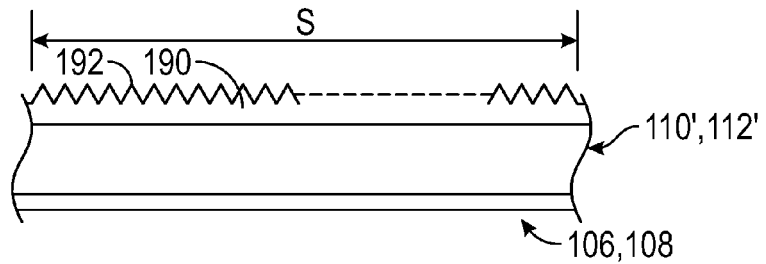
FIG. 5 is a detail of a modification of the embodiment of FIGS. 3 and 4.

In an embodiment, the excitation segments 110, 112 may have a length indicated in FIGS. 3 and 5 by the distance S. That distance S preferably is equal to $\pi \times (D+L)$, where D is the diameter of the wheels 138, 140, 144, and 146 and L is the center-to-center spacing between wheels 138, 140 and between wheels 144, 146 on the trucks 142, 148. With this minimum rail length S, both wheels 138, 140 and 144, 146 of each pair of wheels may be scanned and imaged by the infrared detector 130 as they roll around their entire circumferences. Energizing the system 100 for the full rotation of the wheels 138, 140, 144, and 146 increases the opportunity to detect a flaw, such as cracks 126, 128, especially if the weight of the railcar 104 or position of the wheels effected the thermal response to the excitation.

Figure 6:
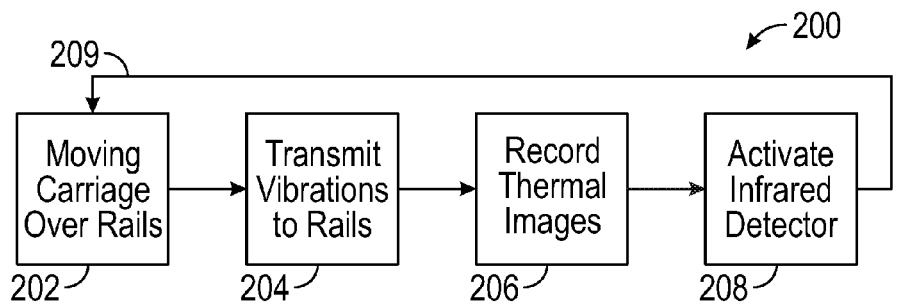
FIG. 6 is a flow chart of a method of operation of the system of FIGS. 1 and 2.

As shown in FIG. 6, in a method of nondestructive evaluation of railroad rails, generally designated 200, utilizing the system 10 of FIGS. 1 and 2, the method begins by moving the carriage 32 having a plurality of wheels 36, 38, 40 over the rails 12, 14 in the direction of arrow A, as indicated in block 202. This movement of the carriage or railcar 32 brings the carriage over a selected one of the test regions 48, so that the infrared cameras 60-70 of the array 58 of the infrared detector 54 are in position to record thermal images 300 of the feet, webs and heads of the rails 12, 14 within the test regions 48 of those rails. As indicated in block 204, vibrations are transmitted at a preselected frequency to the test regions 48, 50 on the rails 12, 14 through the wheels 36, 38, 40 by the source of vibration 46 mounted on the carriage 32. The source of vibration 46 may be an ultrasonic transducer 82, and/or contact with the rails 12, 14 by the segmented peripheries 85, 86, 92 of one or more of the wheels 36, 38, 40 (which, in embodiments, may have the appearance of grooves 192 of FIG. 5). The vibrations may cause an increase in temperature of the rails 12, 14 at locations of flaws 52 in the test region 48.

As indicated in block 206, the thermal images 300 (FIG. 8) may be recorded by an infrared detector, generally designated 54, in the test region 48 which detect and record the increase in temperature at the locations of the flaws 52. These increases in temperature appear as bright spots 302 on the thermal images 300 recorded by the infrared detector 54. As indicated in block 208, the controller 56 may actuate the infrared detector 54 to record the thermal images 300 of the vibrations impacting the test regions 48, 50 and store the thermal images recorded by the infrared detector. These images may be reviewed later to make a determination on whether a repair is necessary. In an alternate embodiment, the images may be transmitted to a remote location and viewed on a display (not shown). As indicated by arrow 209, the process 200 may be repeated by moving the carriage 32 in the direction of arrow A to the next contiguous test region 50 to repeat the process of blocks 204-208.

Figure 7:
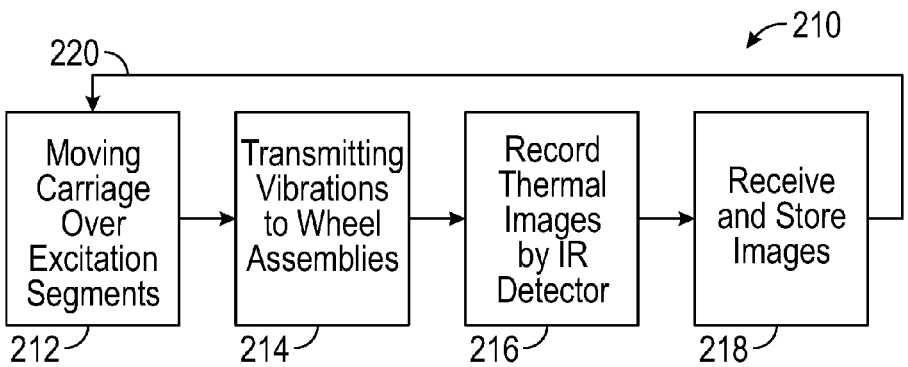
FIG. 7 is a flow chart of a method of operation of the system of FIGS. 3 and 4.

As shown in FIG. 7, the method of FIGS. 3 and 4 is shown by a flow chart 210. In the method indicated at 210, block 212 indicates the initiation of the process by moving a carriage 104, which may take the form of a railcar, over the excitation segments 110, 112 of a pair of rails 106, 108, respectively, in the direction of arrow B. This motion moves the wheels 138, 140, 144, and 146 over the excitation segments 110, 112 so that the wheels are in position to be imaged by the infrared cameras 168-180 of the array 150 of infrared detector 130. As indicated in block 214, vibrations may be transmitted at a preselected frequency by a source of vibrations 114, 116, or alternately, by ridges 192 (FIG. 5), to the wheels 138, 140, 144, and 146 of wheel assemblies 102. The vibrations may be transmitted at test regions 118-124, which may be the portions of the wheels 138, 140, 144, and 146 that are in physical contact with the excitation segments 110, 112 of the rails 106, 108.

As indicated in block 216, an infrared detector 130 may be actuated to record thermal images 300 of the test regions 118-124 to detect the increase in temperature at the locations of the flaws 126, 128. And, as indicated in block 218, a controller 132 may actuate the infrared detector 130 to record the thermal images 300 of the vibrations impacting the test regions and store the thermal images recorded by the infrared detector. As indicated by arrow 220, the process 210 may be repeated by moving a subsequent railcar 104, or a subsequent wheel or wheel truck, over the excitation segments 110, 112 so that the wheels thereof are in position to be imaged by the infrared cameras 168-180.

The system shown in FIGS. 1-5, and the method illustrated schematically in FIGS. 6 and 7, may be used to detect flaws using a nondestructive evaluation process and system for rail vehicles and rail systems that may include railroads, trolleys, and other systems. The advantage of the systems 10, 100 and methods 200, 210 shown in the figures and described herein is that the testing may be done without removal of the tested components for remote testing, and may be performed on a kinetic reference frame; that is, a reference frame in which one of either the test object or the testing apparatus is moving relative to the other. With the system 10 shown in FIGS. 1 and 2, it is the testing apparatus carried in carriage or railcar 32 that is moving relative to the stationary rails 12, 14 that are inspected. Conversely, with the system shown in FIGS. 3, 4, and 5, the test object is in the form of the wheels 138, 140, 144, and 146 of a railcar 104 that are moved past a stationary system 100 and the wheels and/or axles are imaged. In a preferred embodiment, with the embodiment of FIGS. 3, 4, and 5, it may be desirable to provide a washing station 198 through which the wheels 138, 140, 144, and 146 pass prior to being imaged by the infrared detector 130. Accordingly, the railcar in FIGS. 3 and 4 travels in the direction of arrow B.

While the systems and methods herein described constitute preferred embodiments of the disclosed nondestructive evaluation system and method for railroad rails, wheels, and axles, it is to be understood that the disclosure is not limited to these precise systems and methods, and that changes may be made therein without departing from the scope of the disclosure.

What is claimed is:

1. A system for nondestructive evaluation of railroad rails, the system comprising:
   a carriage including a plurality of wheels movably supporting the carriage on the rails;
   a source of vibration mounted on the carriage and connected to the carriage to transmit vibrations of a preselected frequency to test regions on the rails through the wheels to cause an increase in temperature of the rails at locations of flaws in the test regions;
   an infrared detector for recording thermal images of the test regions to detect the increase in temperature at the locations of flaws; and
   a controller connected to the infrared detector actuate the infrared detector to record the thermal images of the vibrations impacting the test regions, and store the thermal images recorded by the infrared detector.

2. The system of claim 1, wherein the infrared detector includes an array of infrared cameras oriented to record images of a head portion of the rails, an inside web portion of the rails, and an outside web portion of the rails in the test regions.

3. The system of claim 1, wherein the source of vibration includes an ultrasonic transducer contacting a component of the carriage and connected such that the controller actuates the ultrasonic transducer to transmit the vibrations to the test regions on the rails.

4. The system of claim 3, wherein the component is selected from the wheels and an axle connected to the wheels and attached to a remainder of the carriage.

5. The system of claim 1, wherein the source of vibration includes one or more of the plurality of wheels having peripheries sufficiently rough to cause the vibrations in the test regions of the preselected frequency when the carriage moves relative to the rails at a preselected speed.

6. The system of claim 5, wherein the peripheries of the one or more of the plurality of wheels have segmented surfaces.

7. The system of claim 5, wherein two or more of the plurality of wheels have peripheries with segmented surfaces arranged to generate the vibrations as the carriage moves relative to the rails that are out of phase with each other, and the preselected frequency is greater than 1 kilohertz.

8. The system of claim 1, wherein the controller includes a data store for storing the recorded thermal images.

9. The system of claim 1, wherein the controller includes a visible light camera connected to be actuated by the controller for photographing the test regions; and the controller is programmed to actuate the visible light camera when a flaw is detected in the rails.

10. The system of claim 1, wherein the controller includes a global positioning system connected to record a location of a flaw in the rails detected by the infrared detector.

11. A system for nondestructive evaluation of a wheel assembly on a railcar, the system comprising:
a pair of rails, each having an excitation segment with a source of vibration connected to transmit vibrations of a preselected frequency to test regions on the wheel assembly to cause an increase in temperature of the wheel assembly at locations of flaws in the test regions;
an infrared detector for recording thermal images of the test regions to detect the increase in temperature at the locations of flaws; and
a controller connected to actuate the infrared detector to record the thermal images of the vibrations impacting the test regions, and store the thermal images recorded by the infrared detector.

12. The system of claim 11, further comprising a visible light camera connected to be actuated by the controller to record an image of the railcar having the wheel assembly for which thermal images are recorded.

13. The system of claim 11, wherein the infrared detector includes an array of infrared cameras positioned to record thermal images of outboard faces of wheels of the wheel assembly and inboard faces of the wheels as the wheels pass over the excitation segments.

14. The system of claim 13, wherein the array of infrared cameras is arranged along a length of the excitation segments sufficient to record images of entire circumferences of two sets of the wheels in a railroad truck.

15. The system of claim 11, wherein the infrared detector includes an array of infrared cameras positioned to record thermal images of axles of the wheel assembly as the axles pass over the excitation segments.

16. The system of claim 11, further comprising a marker connected to be actuated by the controller, for marking the wheel assemblies in which flaws have been detected.

17. The system of claim 11, wherein the source of vibration includes an ultrasonic transducer connected to transmit the vibrations to the excitation segments of the rails, and connected to be actuated by the controller to transmit the vibrations to the test regions of the wheel assemblies when the test regions contact the excitation segments.

18. The system of claim 11, wherein the source of vibration includes the excitation segments having upper surfaces with grooves shaped such that movement of the wheels of the railcar over the grooves at a predetermined speed causes the vibrations in the wheel assemblies.

19. A method for nondestructive evaluation of railroad rails, the method comprising:
moving a carriage having a plurality of wheels on the rails;
transmitting vibrations of a preselected frequency to test regions on the rails through the wheels by a source of vibration mounted on the carriage, the vibrations causing an increase in temperature of the rails at locations of flaws in the test regions;
recording thermal images by an infrared detector of the test regions to detect the increase in temperature at the locations of flaws; and
actuating the infrared detector by a controller to record the thermal images of the vibrations impacting the test regions, and storing the thermal images recorded by the infrared detector.

20. A method for nondestructive evaluation of a wheel assembly on a railcar, the method comprising:
moving a carriage over excitation segments of a pair of rails;
transmitting vibrations of a preselected frequency by a source of vibration to test regions on the wheel assembly to cause an increase in temperature of the wheel assembly at locations of flaws in the test regions;
recording by an infrared detector thermal images of the test regions to detect the increase in temperature at the locations of flaws; and
actuating by a controller the infrared detector to record the thermal images of the vibrations impacting the test regions, and storing the thermal images recorded by the infrared detector.

* * * * *